(12) United States Patent
Consiglio

(10) Patent No.: US 11,224,691 B2
(45) Date of Patent: Jan. 18, 2022

(54) SYSTEM AND METHOD FOR PREDICTING MOTOR WEAR OUT IN INFUSION SYSTEMS

(71) Applicant: KONINKLIJKE PHILIPS N.V., Eindhoven (NL)

(72) Inventor: Ronald Paul Consiglio, Clermont, FL (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 322 days.

(21) Appl. No.: 16/333,283

(22) PCT Filed: Sep. 22, 2017

(86) PCT No.: PCT/IB2017/055757
§ 371 (c)(1),
(2) Date: Mar. 14, 2019

(87) PCT Pub. No.: WO2018/060821
PCT Pub. Date: Apr. 5, 2018

(65) Prior Publication Data
US 2019/0240402 A1  Aug. 8, 2019

Related U.S. Application Data

(60) Provisional application No. 62/401,320, filed on Sep. 29, 2016.

(51) Int. Cl.
*A61M 5/168* (2006.01)
*A61M 5/145* (2006.01)
(Continued)

(52) U.S. Cl.
CPC ........ *A61M 5/16831* (2013.01); *A61M 5/142* (2013.01); *A61M 5/1452* (2013.01); *G16H 40/40* (2018.01); *A61M 5/007* (2013.01); *A61M 2205/3306* (2013.01); *A61M 2205/3317* (2013.01); *A61M 2205/3365* (2013.01); *A61M 2205/702* (2013.01); *H02P 2203/09* (2013.01)

(58) Field of Classification Search
CPC .................... A61M 5/16831; A61M 5/142; H02P 2203/09
USPC .................... 318/400.4, 400.37, 400.01, 700
See application file for complete search history.

(56) References Cited

U.S. PATENT DOCUMENTS 6,362,591 B1  3/2002  Moberg
9,670,917 B2 * 6/2017  Nakajima ............... F04B 17/03
(Continued)

FOREIGN PATENT DOCUMENTS

| GB | 2428745 | 2/2007 |
|---|---|---|
| WO | 2010/076275 | 7/2010 |
| WO | 2003089034 | 10/2013 |

*Primary Examiner* — David Luo

(57) ABSTRACT

A rotary drive for a medical device (10) includes a rotary motor (14) including a rotor (26). A rotary motion encoder (34) is connected to the rotor. The rotary motion encoder is configured to generate a number of encoder steps measuring a rotational distance of the rotor. At least one electronic processor (18) is programmed to determine at least one of a slippage value of the rotary motor measured during motor operation and a coasting value of the rotary motor measured after stopping motor operation based on comparison of an actual count of encoder steps and an expected count of encoder steps.

15 Claims, 3 Drawing Sheets

(51) Int. Cl.
*A61M 5/142* (2006.01)
*G16H 40/40* (2018.01)
*A61M 5/00* (2006.01)

(56) References Cited

U.S. PATENT DOCUMENTS

2012/0078170 A1 3/2012 Smith
2013/0303989 A1 11/2013 Favreau

* cited by examiner

SYSTEM AND METHOD FOR PREDICTING MOTOR WEAR OUT IN INFUSION SYSTEMS

CROSS REFERENCE TO RELATED APPLICATIONS

This application is the U.S. National Phase application under 35 U.S.C. § 371 of International Application No. PCT/IB2017/055757 filed Sep. 22, 2017, published as WO 2018/060821 on Apr. 5, 2018, which claims the benefit of U.S. Provisional Patent Application No. 62/401,320 filed Sep. 29, 2016. These applications are hereby incorporated by reference herein.

FIELD

The following relates generally to the radiology arts, medical infusion arts, infusion pump arts, and related arts.

BACKGROUND

Currently, infusion pumps used in both hospital and home use motor systems to pressurize liquid for delivery to the patient. These motor systems are subject to wear. These types of pumps perform checks on the health of the drive system at start-up and allow or disallow the pump to be used by the clinician. There is no predictive element to this decision.

Infusion pumps for general use in the hospital cannot safely be used in the MRI environment as they pose serious safety risks to clinicians and patients. Special pumps have been developed specifically for MR use, but these pose their own risks as these pumps are different to those the clinician is familiar with and vital seconds can be lost in the case of an emergency as clinicians struggle to perform unfamiliar actions.

Improvements disclosed herein address the foregoing and other disadvantages of existing infusion pump systems, methods, and the like.

BRIEF SUMMARY

In accordance with one illustrative example, a rotary drive for a medical device includes a rotary motor with a rotor. A rotary motion encoder, connected to the rotor, is configured to generate a number of encoder steps measuring a rotational distance of the rotor. At least one electronic processor is programmed to determine at least one of a slippage value of the rotary motor measured during motor operation and a coasting value of the rotary motor measured after stopping motor operation based on a comparison of an actual count of encoder steps and an expected count of encoder steps.

In accordance with another illustrative example, a method of using a medical device in a Magnetic Resonance environment is provided. The method includes: with a rotary motion encoder, generating a number of encoder steps measuring a rotational distance of a rotor of a rotary motor; and with at least one processor, determining at least one of a slippage value of the rotary motor measured during motor operation and a coasting value of the rotary motor measured after stopping motor operation based on a comparison of an actual count of encoder steps and an expected count of encoder steps.

In accordance with another illustrative example, a rotary drive for a medical pump includes a non-magnetic rotary motor with a rotor. A rotary motion encoder is connected to the rotor. The rotary motion encoder is configured to generate a number of encoder steps measuring a rotational distance of the rotor. At least one electronic processor is programmed to determine each of a slippage value of the rotary motor measured during motor operation and a coasting value of the rotary motor measured after stopping motor operation based on a calculated difference of an actual count of encoder steps and an expected count of encoder steps.

One advantage resides in reducing MR interference generated by a medical device in an MR environment.

Another advantage resides in detecting excessive motor wear for a motor in a medical device.

Another advantage resides in detecting excessive motor wear using measurement of motor characteristics indicative of motor wear.

Another advantage resides preventing a medical device from turning on when a motor of the medical device is unreliable due to excessive wear.

Further advantages of the present disclosure will be appreciated to those of ordinary skill in the art upon reading and understand the following detailed description. It will be appreciated that a given embodiment may provide none, one, two, or more of these advantages.

BRIEF DESCRIPTION OF THE DRAWINGS

The present disclosure may take form in various components and arrangements of components, and in various steps and arrangements of steps. The drawings are only for purposes of illustrating the preferred embodiments and are not to be construed as limiting the invention.

DETAILED DESCRIPTION

The following relates to monitoring motor wear in MR-compatible syringe pumps or other MR-compatible devices that employ non-magnetic motors. In such medical devices, a non-magnetic rotary motor is used to provide motive drive, e.g. to drive the piston that pushes on the syringe plunger so as to deliver the fluid medication, or to drive the pumping membrane of the fluid pump of a volumetric infusion pump, or so forth. In the case of infusion pumps, for certain types of medications, such as vasopressors that cause constriction of blood vessels to elevate blood pressure, the interruption of delivery of medication for even a few seconds can adversely impact patient health. In syringe pumps employing a normal magnetic motor, it is known to monitor operation of the motor to detect a failure. However, this monitoring does not predict motor failure and hence can lead to interruption of critical medication.

The following discloses a system and method to monitor the response of the non-magnetic rotary motor to assess motor wear. In an illustrative ultrasonic motor, an applied electrical sine wave induces vibration in a stator element that in turn drives the rotor. A rotary motion encoder is used to monitor rotation in units of encoder steps. A given number of cycles of the electrical sine wave is expected to induce a certain rotational "distance" measured in encoder steps. However, if the motor is beginning to wear down then slippage may occur such that the measured number of encoder steps for a given number of electrical cycles decreases. In general, the wear down is expected to be due to degradation of friction material providing the rotor coupling.

Another effective metric of motor wear disclosed herein is the amount of coasting that occurs after cessation of the driving electrical sine wave. In particular, as the friction material wears down the rotor has been found to coast for some time after the sine wave is turned off. This coasting can be measured as the number of encoder steps that occur after the electrical sine wave is turned off—more coasting encoder steps implies greater motor wear.

The disclosed motor wear sensor can be calibrated using empirical lifetime tests, i.e. measuring the slippage and coasting as a function of motor usage time. In a contemplated embodiment for providing timely guidance as to when a motor has excessive wear sufficient to compromise reliability, when slippage and/or coasting exceeds some first threshold a warning is provided to replace or service the motor. If a second threshold is exceeded then the infusion pump may be prevented from starting up until service is performed.

Figure 1:
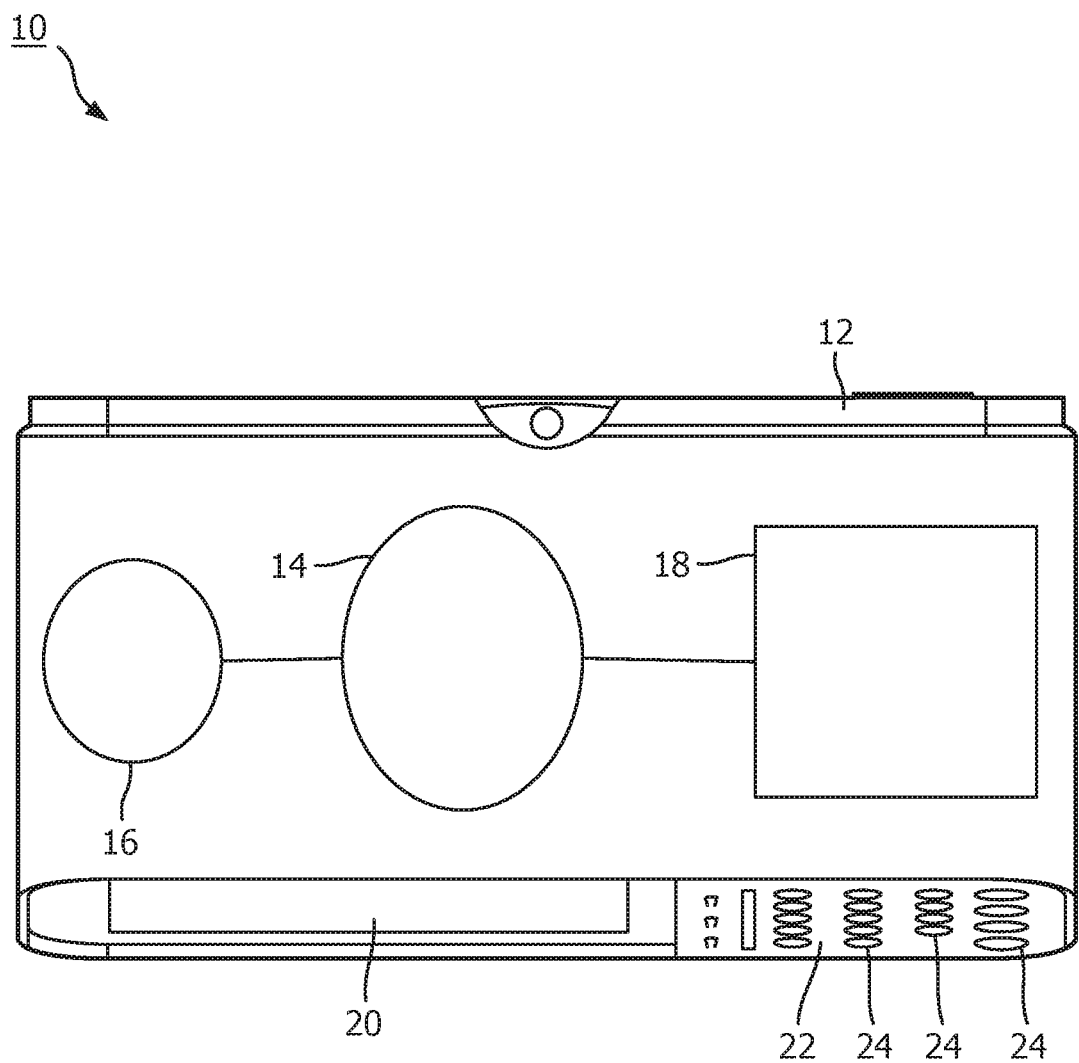
FIG. 1 diagrammatically illustrates a top view of medical device in accordance with one aspect.

With reference now to FIG. 1, a schematic illustration of a top view of a medical device 10 is shown. The illustrative medical device 10 is an infusion pump that includes a housing 12 that encloses a fluid pump 14, a power source (or power converter, e.g. converting 110 Vac to a device drive power) 16, and at least one electronic processor 18. As illustrated in FIG. 1, a "top" portion of the housing 12 is removed, so that the internal components disposed therein are visible. The fluid pump 14 is configured to pump intravascular (IV) fluid from an IV fluid bag into tubing feeding into a cannula or other coupling to a patient vein (for intravenous infusion) or artery (for arterial infusion) to deliver medication to a patient. In an alternative syringe pump embodiment, the fluid pump 14 comprises a syringe loaded into the syringe pump and a motor/piston arrangement for controlled operation of the plunger of the syringe to deliver IV fluid flow at a programmed flow rate. The motor of the fluid pump 14 is powered by the power source 16 (e.g., a battery). The at least one processor 18 is programmed to control operations of the infusion pump 10, as described in more detail below.

The medical device 10 optionally also includes a display 20 configured to display details of operations of the medical device 10, and/or a keypad 22 or other user input device, e.g. disposed adjacent the display 20. The illustrative keypad 22 includes a plurality of keys 24, but other input devices such as knobs, dials, or so forth are contemplated.

Figure 2:
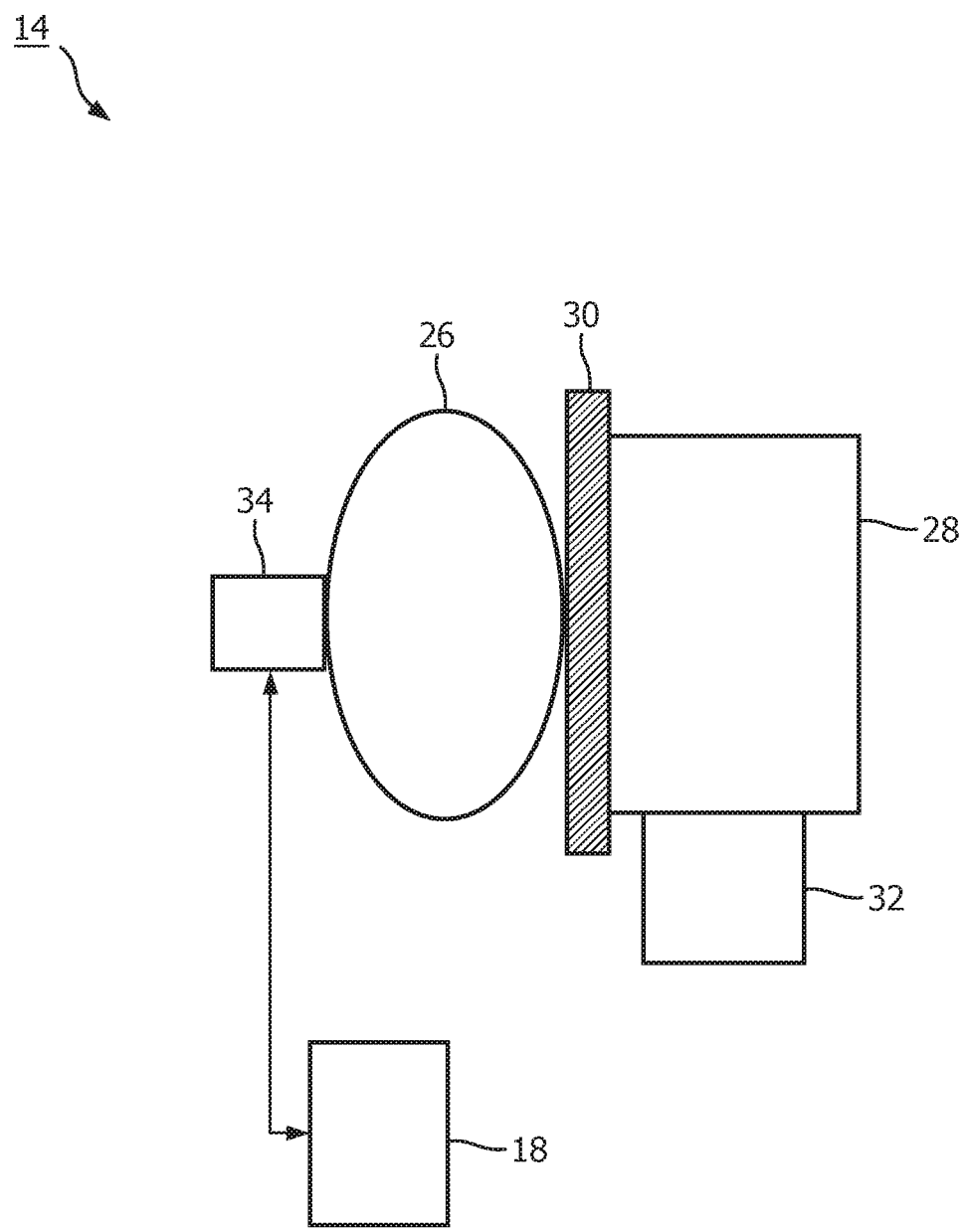
FIG. 2 diagrammatically illustrates a first operative state of the medical device of FIG. 1.
Figure 3:
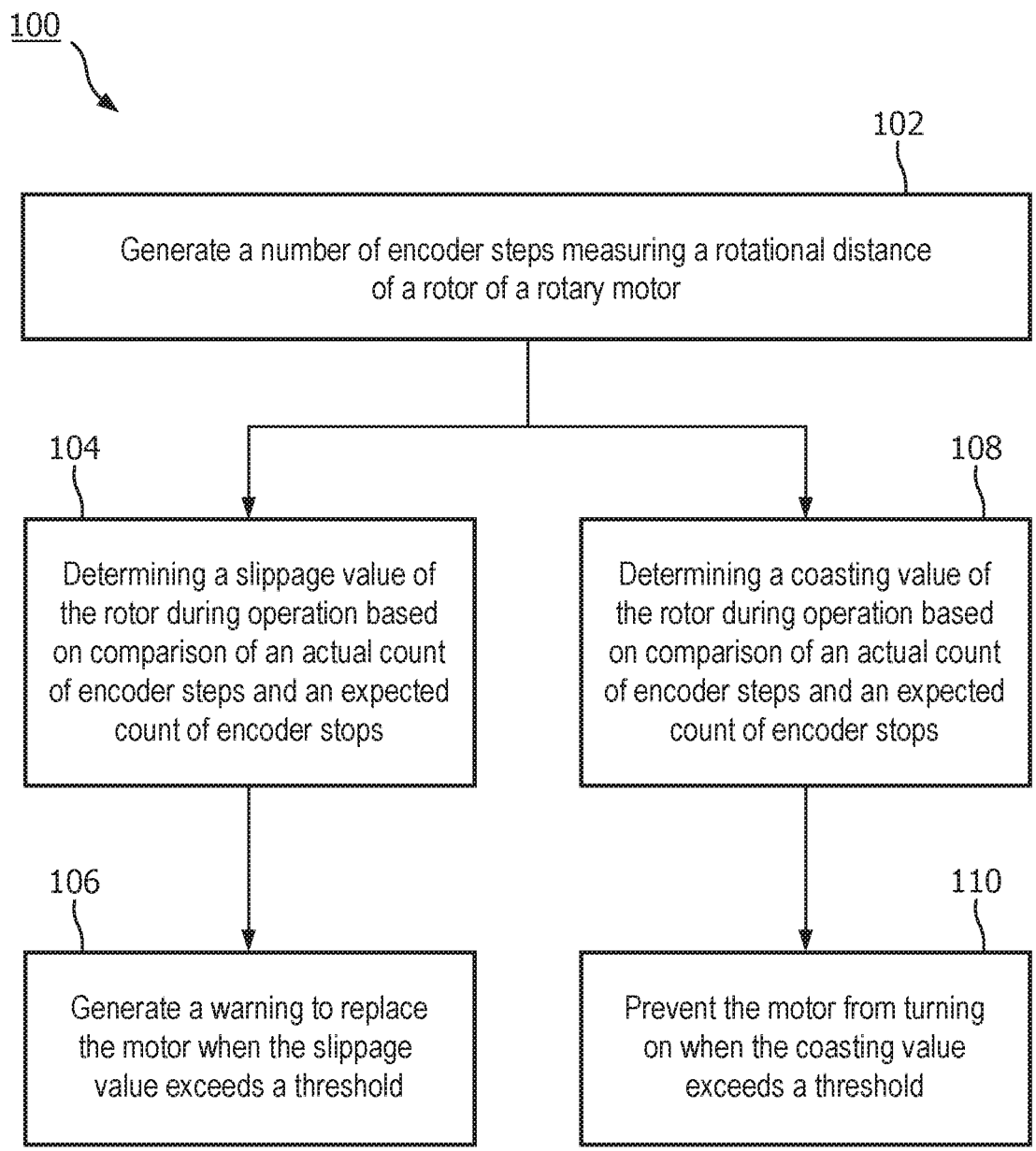
FIG. 3 diagrammatically illustrates a medical device illumination method suitably performed using the medical device of FIG. 1.

With reference now to FIG. 2, and with continuing reference to FIG. 1, an illustrative ultrasonic motor is diagrammatically shown, which may serve as the motor for the fluid pump 14 of the infusion pump 10. The ultrasonic motor includes a rotor 26 and a stator 28. The rotor 26 is coupled to the stator 28 with a friction material 30. FIG. 2 illustrates the motor components 26, 28, 30 diagrammatically; as is known in the art, there are various configurations by which rotary motion of the rotor 26 may be induced by application of a sine wave or other motive electrical signal to the stator 28. A current source 32 is configured to input an electrical sine wave to the stator 28, which causes the stator to drive the rotor 26 (and therefore run the motor 14). The current source 32 may be powered, for example, by the power source 16 of FIG. 1.

A rotary motion encoder 34 is operatively connected with the rotor 26. The rotary motion encoder 34 is configured to generate a number of encoder steps measuring a rotational distance of the rotor 26. For example, when the rotor completes one revolution, the rotary motion encoder 34 is configured to count the revolution as one encoder step. However, it will be appreciated that any rotational distance of the rotor 26 (e.g., a half-revolution, 2 revolutions, 10 revolutions, and the like) can be considered an encoder step. The rotary encoder 34 may use any suitable MR-compatible technology, e.g. optical encoding, conductive encoding, or so forth. A magnetic encoding may alternatively be used if the medical device is used in an environment permitting use of magnetic or magnetized materials.

In some embodiments, the at least one electronic processor 18 is programmed to determine a slippage value of the rotary motor measured during motor operation and/or a coasting value of the rotary motor measured after stopping motor operation based on comparison (i.e., a calculated difference) of an actual count of encoder steps and an expected count of encoder steps. For example, if the motor 14 is beginning to wear down, then slippage may occur such that the measured number of encoder steps for a given number of electrical cycles decreases. In general, the wear down is expected to be due to degradation of friction material 30 providing the coupling between the rotor 26 and the stator 28, although other wear mechanisms are contemplated, e.g. plastic deformation of constituent materials.

In some examples, a slippage value is determined for the motor 14. To do so, the at least one processor 18 is programmed to receive the number of encoder steps from the rotary motion encoder 34, and compared the received number of encoder steps to an expect count of encoder steps that is programmed into the at least one processor. When the actual count falls below the expected count, a greater wear status of the motor 14 is determined. It will be appreciated that the wear status of the motor 14 constitutes a wear status of the friction material 30. A greater wear status is indicative of the friction material 30 being worn down, and thus a higher slippage value is determined. When the friction material 30 is worn down too much, such as when the measured number of encoder steps exceeds a first threshold value, the at least one processor 18 is programmed to generate or issue a warning to replace the motor 14. This warning can be displayed on the display 20.

In other examples, a coasting value (i.e., the amount of coasting that occurs after cessation of the driving electrical sine wave from the current source 32 to the stator 28) is determined for the motor 14. To do so, the at least one processor 18 is programmed to receive the number of encoder steps from the rotary motion encoder 34, and compared the received number of encoder steps to an expect count of encoder steps that is programmed into the at least one processor. When the actual count is higher than the expected count, this implies coasting (i.e. additional rotation of the rotor due to wear-induced friction reduction), and a greater wear status of the motor 14 is determined. Typically, the wear status of the motor 14 constitutes a wear status of the friction material 30. A greater wear status is indicative of the friction material 30 being worn down, and thus a higher coasting value is determined. When the friction material 30 is worn down too much, such as when the measured number of encoder steps exceeds a second threshold value during the coasting measurement performed after cessation of electrical drive power, the at least one processor 18 is programmed to prevent the motor 14 from turning on (i.e., by disabling the power source 16). Similar wear status responses can be employed in embodiments in which the wear status is assessed by monitoring for slippage during motor operation.

It will be appreciated that the illustrative medical device 10 (i.e., the illustrative infusion pump 10) is configured for use in an MR environment to avoid generating MR interference. To prevent generating MR interference, the components of the infusion pump 10, in particular the rotary motor 14, are preferably made from non-magnetic materials.

With reference now to FIG. 4, a method 100 of using a medical device 10 in an MR environment is shown. At step 102, a number of encoder steps measuring a rotational distance of a rotor 26 of a rotary motor 14 is generated with a rotary motion encoder 36. At step 104, a slippage value of the rotary motor 14 measured during motor operation is determined based on a comparison of an actual count of encoder steps and an expected count of encoder steps. At step 106, a warning is generated to replace the motor 14 when the measured slippage value exceeds a first threshold. At step 108, a coasting value of the rotary motor measured after stopping motor operation is determined based on comparison of an actual count of encoder steps and an expected count of encoder steps. At step 110, the rotary motor 14 is prevented from turning on when the measured coasting value exceeds a second threshold. It will be appreciated that a given embodiment may monitor either slippage (steps 104, 106), or coasting (steps 108, 110), or may perform both monitoring operations (all of steps 104, 106, 108, 110).

The expected number of encoder steps for slippage (or for coasting) can be determined by performing empirical tests on bench test motors, either installed in a test medical device or in a wear testing jig that provides the drive power and a motor load equivalent to that of the syringe plunger piston, fluid pump membrane, or other load operated by the in-service motor. Optionally, accelerated life testing techniques can be used to expedite the tests, e.g. employing elevated temperature to induce wear at a known acceleration compared with normal operation. The thresholds for providing remediation recommendations or interlocks (e.g. recommendation to replace the motor or the entire medical device, or interlocking to prevent operation of a device whose reliability is compromised by excessive motor wear) can also be set using these empirical tests, by running the motors to failure and providing a suitable cushion in the threshold values.

It will be appreciated that the illustrative data processing or data interfacing components of the medical device 10 may be embodied as a non-transitory storage medium storing instructions executable by an electronic processor (e.g. the at least one electronic processor 18) to perform the disclosed operations. The non-transitory storage medium may, for example, comprise a hard disk drive, RAID, or other magnetic storage medium; a solid state drive, flash drive, electronically erasable read-only memory (EEROM) or other electronic memory; an optical disk or other optical storage; various combinations thereof; or so forth.

The disclosure has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A rotary drive for a medical device, the rotary drive comprising:
    a rotary motor including a rotor;
    a rotary motion encoder connected to the rotor, the rotary motion encoder being configured to generate a number of encoder steps measuring a rotational distance of the rotor; and
    at least one electronic processor programmed to:
        determine at least one of a slippage value of the rotary motor measured during motor operation and a coasting value of the rotary motor measured after stopping motor operation based on a comparison of an actual count of encoder steps and an expected count of encoder steps; and
        determine a wear status of the rotary motor based on at least one of the determined slippage value and the determined coasting value.

2. The rotary drive according to claim 1, wherein the at least one electronic processor is programmed to determine each of a slippage value of the rotary motor measured during motor operation and a coasting value of the rotary motor measured after stopping motor operation based on a comparison of an actual count of encoder steps and an expected count of encoder steps.

3. The rotary drive according to claim 1, wherein the at least one electronic processor is programmed to determine each of a slippage value of the rotary motor measured during motor operation and a coasting value of the rotary motor measured after stopping motor operation based on a calculated difference of an actual count of encoder steps and an expected count of encoder steps.

4. The rotary drive according to claim 1, wherein the at least one electronic processor is programmed to determine a wear status of the rotary motor based on a determined slippage value wherein a lower actual count compared with the expected count indicates greater wear status.

5. The rotary drive according to claim 1, wherein the at least one electronic processor is programmed to determine a wear status of the rotary motor based on a determined coasting value wherein a higher actual count compared with the expected count indicates greater wear status.

6. The rotary drive according claim 5, wherein the at least one electronic processor is further programmed to:
    generate a warning to replace the motor when at least one of the measured slippage value and the measured coasting value exceeds a first threshold; and
    prevent the rotary motor from turning on when at least one of the measured slippage value and the measured coasting value exceeds a second threshold.

7. The rotary drive of claim 1, wherein the rotary motor is non-magnetic, wherein the rotor is coupled to a stator with a friction material, and the non-magnetic rotary motor further includes:
    a current source configured to input an electrical sine wave to the stator to drive the rotor.

8. A medical pump comprising the rotary drive of claim 1, wherein the rotary motor is non-magnetic.

9. A method of using a medical device in a Magnetic Resonance environment, the method comprising:
    with a rotary motion encoder, generating a number of encoder steps measuring a rotational distance of a rotor of a rotary motor;
    with at least one processor, determining at least one of a slippage value of the rotary motor measured during motor operation and a coasting value of the rotary motor measured after stopping motor operation based on a comparison of an actual count of encoder steps and an expected count of encoder steps; and with the at least one processor; determining a wear status of the rotary motor based on at least one of the determined slippage value and the determined coasting value.

10. The method according to claim 9, further including:
with the at least one electronic processor, determining each of a slippage value of the rotary motor measured during motor operation and a coasting value of the rotary motor measured after stopping motor operation based on a comparison of an actual count of encoder steps and an expected count of encoder steps.

11. The method according to claim 9, further including:
with the at least one electronic processor, determining each of a slippage value of the rotary motor measured during motor operation and a coasting value of the rotary motor measured after stopping motor operation based on a calculated difference of an actual count of encoder steps and an expected count of encoder steps.

12. The method according to claim 9, further including:
with the at least one electronic processor, determining a wear status of the rotary motor based on a determined slippage value wherein a lower actual count compared with the expected count indicates greater wear status.

13. The method according claim 12, further including, with the at least one electronic processor:
generating a warning to replace the motor when at least one of the measured slippage value and the measured coasting value exceeds a first threshold; and
preventing the rotary motor from turning on when at least one of the measured slippage value and the measured coasting value exceeds a second threshold.

14. The method according to claim 9, further including:
with the at least one electronic processor, determining a wear status of the rotary motor based on a determined coasting value wherein a higher actual count compared with the expected count indicates greater wear status.

15. The rotary drive of claim 9, wherein the rotary motor is non-magnetic, wherein the rotor is coupled to a stator with a friction material, and the method further includes
with a current source of the non-magnetic rotary motor, inputting an electrical sine wave to the stator to drive the rotor.

* * * * *